(12) United States Patent
Zajas

(10) Patent No.: US 9,125,713 B2
(45) Date of Patent: Sep. 8, 2015

(54) DENTAL FLOSS DISPENSER BUSINESS CARD

(76) Inventor: Paul J. Zajas, Mesa, AZ (US)

( * ) Notice: Subject to any disclaimer, the term of this patent is extended or adjusted under 35 U.S.C. 154(b) by 482 days.

(21) Appl. No.: 12/341,522

(22) Filed: Dec. 22, 2008

(65) Prior Publication Data

US 2010/0154814 A1    Jun. 24, 2010

(51) Int. Cl.
*A61C 15/00* (2006.01)
*A61C 15/04* (2006.01)

(52) U.S. Cl.
CPC ............. *A61C 15/043* (2013.01); *A61C 15/04* (2013.01)

(58) Field of Classification Search
CPC .... A61C 15/00; A61C 15/043; A61C 15/046; A61C 15/04
USPC .................................................. 132/321–329
See application file for complete search history.

(56) References Cited

U.S. PATENT DOCUMENTS

| | | | |
|---|---|---|---|
| 3,446,260 A * | 5/1969 | Osher | 150/147 |
| 4,162,688 A | 7/1979 | Tarrson et al. | |
| 4,327,755 A | 5/1982 | Endelson | |
| 4,881,560 A * | 11/1989 | Blank et al. | 132/324 |
| D309,959 S | 8/1990 | Endelson et al. | |
| 5,076,423 A | 12/1991 | Russack | |
| 5,649,659 A * | 7/1997 | Saunders | 225/39 |
| 5,678,580 A | 10/1997 | Sherman | |
| 5,722,439 A | 3/1998 | Endelson | |
| 5,787,907 A | 8/1998 | Endelson | |
| 5,875,796 A * | 3/1999 | Silver-Isenstadt et al. | 132/311 |
| 6,047,712 A | 4/2000 | Blades et al. | |
| D491,313 S | 6/2004 | Schrott | |
| 6,832,615 B2 * | 12/2004 | Hensel | 132/321 |
| 7,546,860 B1 * | 6/2009 | Mehdizadeh | 150/138 |
| 7,665,600 B1 * | 2/2010 | Griffin | 206/63.5 |
| 2003/0101063 A1 * | 5/2003 | Sexton et al. | 705/1 |

OTHER PUBLICATIONS

PCT/US2009/069262 International Search Report dated Mar. 11, 2010.

* cited by examiner

*Primary Examiner* — Robyn Doan
(74) *Attorney, Agent, or Firm* — Scott A. Hill; The Hill Law Firm, PLC

(57) ABSTRACT

A dispenser includes a dispenser body and a sleeve carried by the dispenser body, wherein the sleeve includes a sleeve opening. A card, such as a business card, is repeatably moveable through the sleeve opening. The dispenser includes a dental floss recess for receiving dental floss. The sleeve covers the dental floss recess.

6 Claims, 6 Drawing Sheets

DENTAL FLOSS DISPENSER BUSINESS CARD

BACKGROUND OF THE INVENTION

1. Field of the Invention

This invention relates to dental floss dispensers.

2. Description of the Related Art

There are many different types of dental floss dispensers, such as those disclosed in U.S. Pat. Nos. 4,162,688, 4,327,755, 4,881,560, 5,722,439, 5,787,907 and 6,047,712, as well as U.S. Design Pat. No. D309,959. It is useful if the dispenser is in a compact form so it is easier and more convenient to carry around. For example, the dental floss dispensers of U.S. Pat. Nos. 4,327,755, 4,881,560, 5,722,439 and 5,787,907, as well as U.S. Design Pat. No. D309,959 are in a compact form so they can be easily carried in a pocket and wallet. However, the dental floss dispensers of U.S. Pat. Nos. 4,162,688 and 6,047,712 are not in a compact form that allows them to be conveniently carried in a pocket and wallet.

Some of these dental floss dispensers mentioned above have a surface which can be used to print indicia, such as business and contact information. Hence, the dental floss dispenser can be used for advertising. However, once the dental floss dispenser is given away, it must be replaced by another one, which is expensive.

BRIEF SUMMARY OF THE INVENTION

The present invention provides a dispenser, which includes a dispenser body and a sleeve carried by the dispenser body, wherein the sleeve includes a sleeve opening. The dispenser includes a card which is repeatably moveable through the sleeve opening. The card is generally a business card, or another type of card which displays indicia.

The dispenser can include many other features. For example, in some embodiments, the dispenser includes a backing positioned between the dispenser body and sleeve. The sleeve can include a sleeve cut-out positioned proximate to the sleeve opening. The sleeve-cut out facilitates the removal of the card from the sleeve. In some embodiments, the dispenser body includes a panel having a dental floss recess. The dispenser body can include a rib extending towards the sleeve. In some embodiments, the dispenser body includes a blade recess which extends through the dental floss recess towards the sleeve. The blade recess can include a dental floss opening. Dental floss is typically positioned within the dental floss recess so the floss extends around the blade recess.

The present invention provides a dispenser, which includes a dispenser body having a dental floss recess and a sleeve which covers the dental floss recess. The dispenser includes a card which is repeatably moveable through the sleeve.

The dispenser can include many other features. For example, in some embodiments, the dispenser includes a backing positioned between the dispenser body and sleeve. The sleeve can include a sleeve cut-out positioned proximate to a sleeve opening. In some embodiments, the dispenser body includes a rib coupled to the sleeve. The dispenser body can include a dental floss recess bounded by a sidewall. In some embodiments, the dispenser body includes a blade recess which extends through the dental floss recess towards the sleeve. The dispenser can include a dental floss blade positioned proximate to the blade recess.

The present invention provides a method, which includes providing a dispenser body which carries dental floss, coupling a sleeve with the dispenser body, and extending a card through the sleeve.

In some embodiments, the step of extending the card through the sleeve includes extending the card through a sleeve opening. The step of coupling the sleeve with the dispenser body can include coupling the sleeve with a rib of the dispenser body.

The method can include many other steps. For example, in some embodiments, the method includes providing a dental floss blade for cutting the floss, wherein the floss is positioned between the blade and card. The method can include positioning a backing between the dispenser body and sleeve. The step of positioning the backing can include coupling the backing with a rib of the dispenser body.

These and other features, aspects, and advantages of the present invention will become better understood with reference to the following drawings and description.

DETAILED DESCRIPTION OF THE INVENTION

Figure 1:
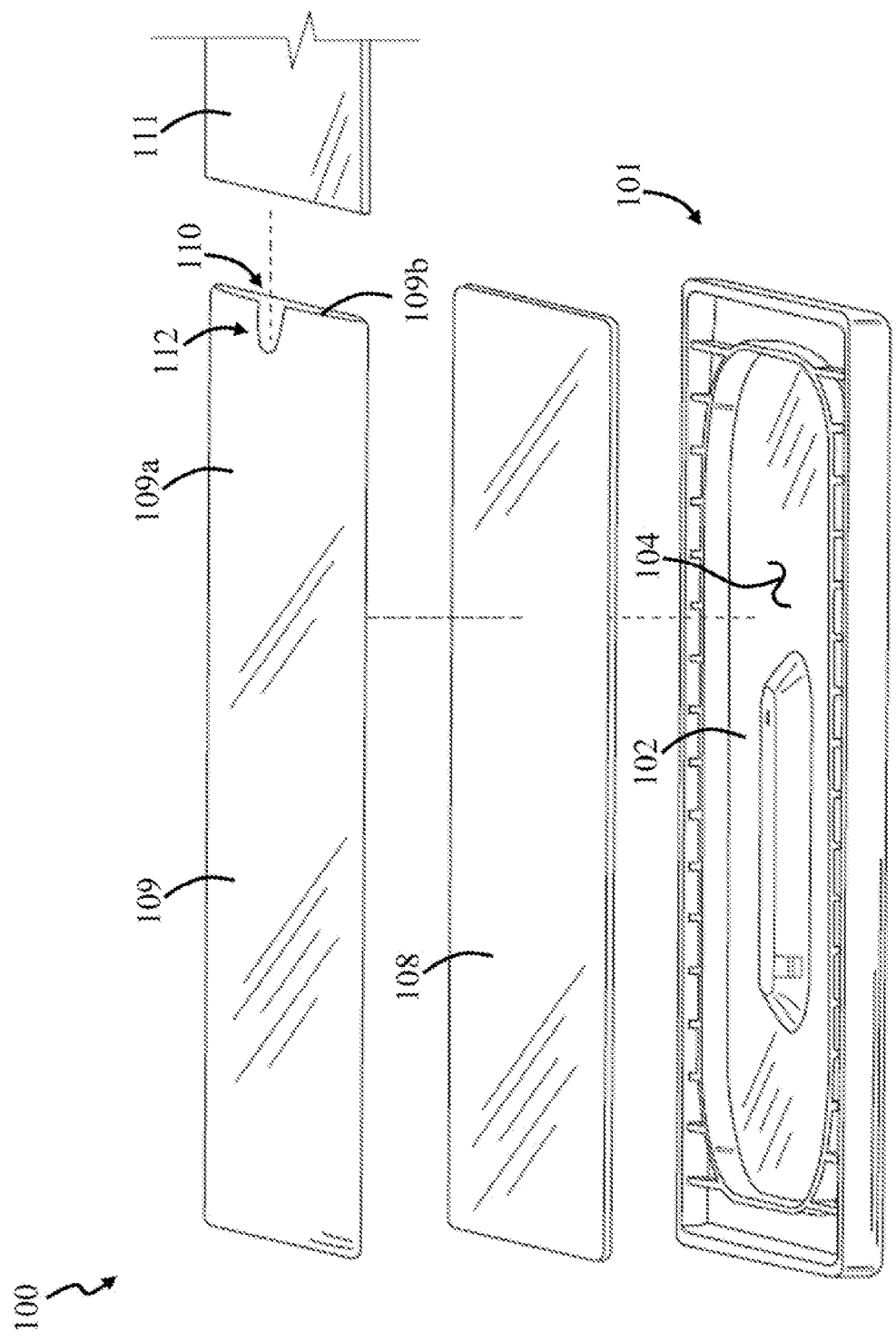
FIG. 1 is an exploded perspective view of a dispenser, in accordance with the invention.
Figure 2A:
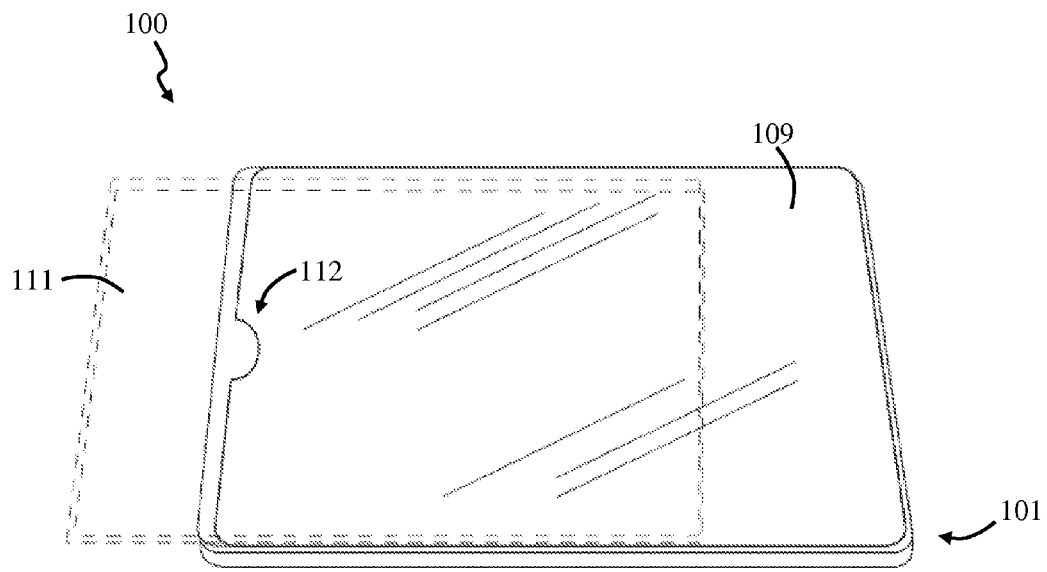
FIGS. 2a and 2b are top and bottom perspective views of the dispenser of FIG. 1.
Figure 2B:
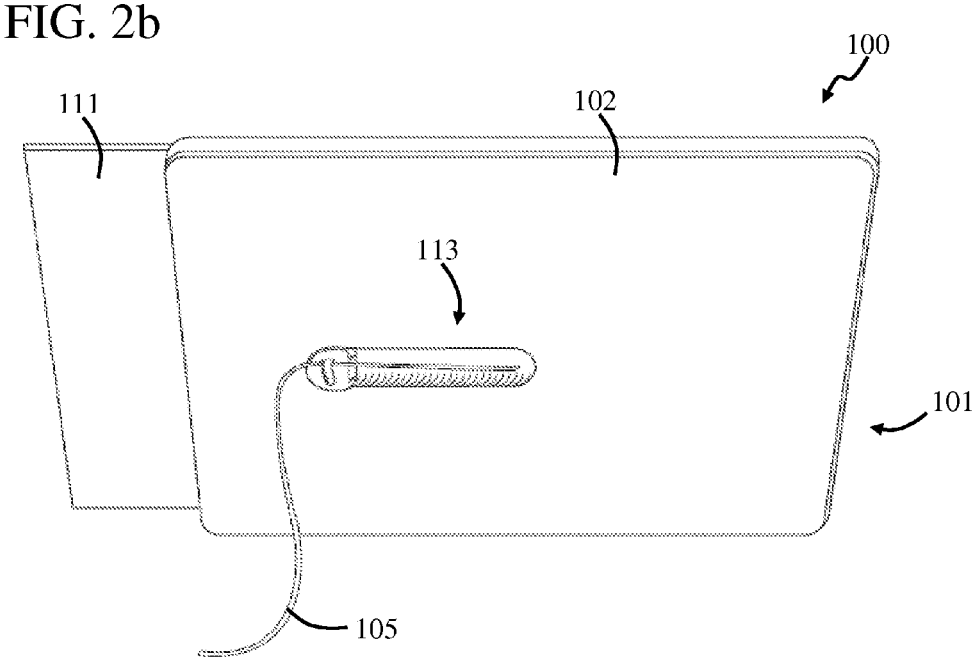

FIG. 1 is an exploded perspective view of a dispenser 100, in accordance with the invention, and FIGS. 2a and 2b are top and bottom perspective views of dispenser 100. In this embodiment, dispenser 100 includes a dispenser body 101. Dispenser body 101 can have many different features. In this embodiment, dispenser body 101 includes a panel 102 (FIG. 2b) with a dental floss recess 104 (FIG. 1).

Figure 3:
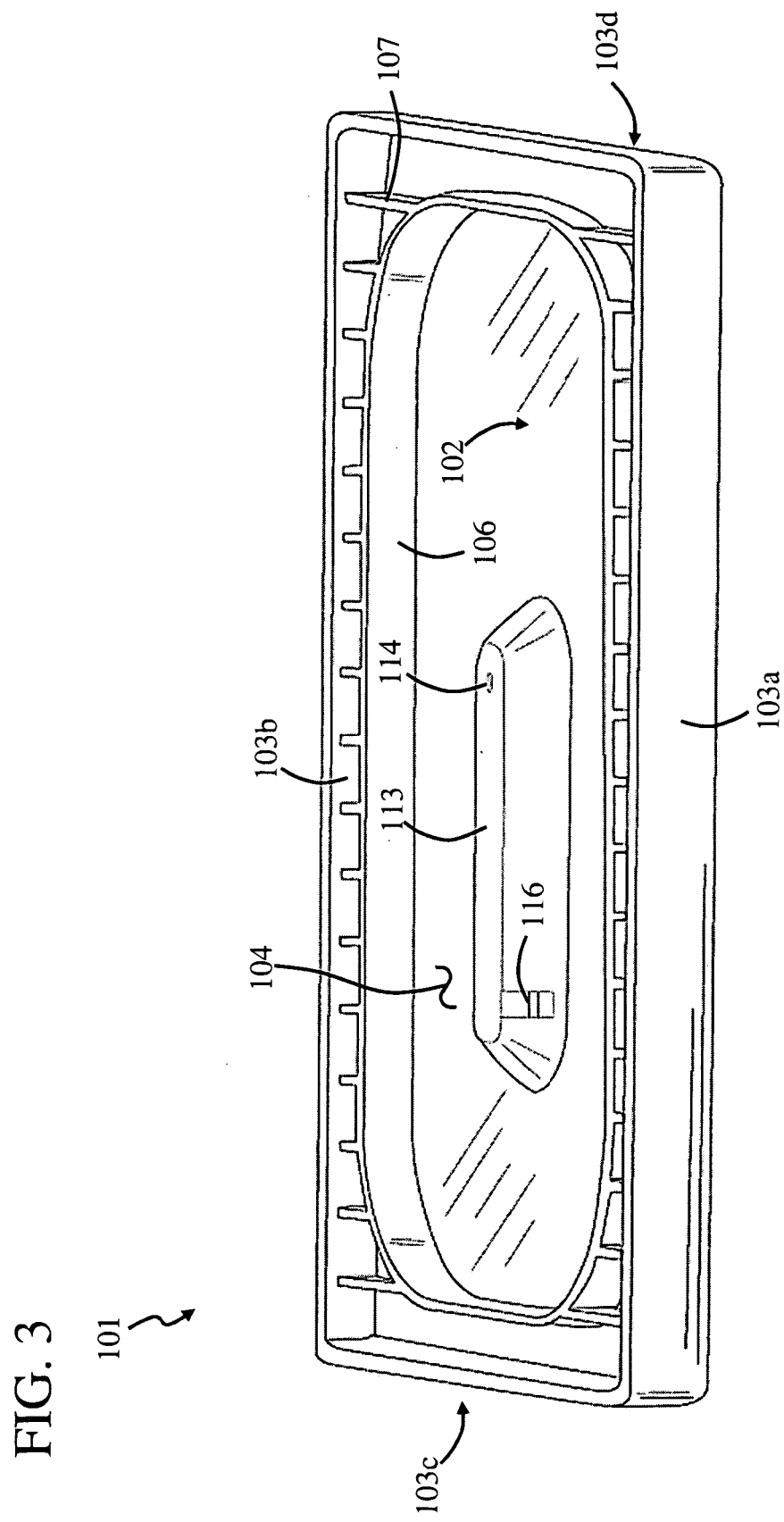
FIG. 3 is a top perspective view of a dispenser body included with the dispenser of FIG. 1.

FIG. 3 is a top perspective view of dispenser body 101. Dispenser body 101 can be many different shapes. In this embodiment, dispenser body 101 is rectangular in shape and includes sidewalls 103a, 103b, 103c and 103d extending from panel 102. Sidewall 103a and 103b are opposed to each other, and panels 103c and 103d are opposed to each other.

In this embodiment, dispenser body 101 includes a dental floss recess 104. Dental floss recess 104 can be positioned at many different locations. In this embodiment, dental floss recess 104 is formed through panel 102 and is positioned between sidewalls 103a, 103b, 103c and 103d. Dental floss recess 104 is useful to receive dental floss 105 (FIG. 2b). In this embodiment, dispenser body 101 includes a dental floss recess sidewall 106 (FIG. 3) which bounds dental floss recess 104 to keep the dental floss therein. Sidewall can have many different shapes, but it is oval in this embodiment, and extends from panel 102.

In this embodiment, dispenser body 101 includes a rib 107 (FIG. 3). Rib 107 can be positioned at many different locations. In this embodiment, rib 107 extends from panel 102.

Further, rib 107 extends along panel 102 and between the sidewalls. For example, in this embodiment, rib 107 extends between sidewalls 103a and 103b. Further, rib 107 extends away from dental floss recess sidewall 106 and sidewall 103b. In particular, rib 107 extends between dental floss recess sidewall 106 and sidewall 103b. It should be noted that dispenser body 101 can include a plurality of ribs, if desired, and these ribs can be positioned in the same or a similar manner to rib 107.

In this embodiment, dispenser 100 includes a backing 108 carried by dispenser body 101. Backing 108 can be positioned at many different locations. In this embodiment, backing 108 is positioned to cover dental floss recess 104. Backing 108 is attached to dispenser body 101. Backing 108 can be attached to dispenser body 101 in many different ways. In this embodiment, backing 108 is attached to sidewall 100 so that dental floss 105 within dental floss recess 104 is bounded by panel 102, dental floss recess sidewall 106 and backing 108. Dental floss recess sidewall 106 is positioned between dental floss 105 and rib 107. Backing 108 can be attached to sidewall 106 in many different ways, such as by using an adhesive. In some embodiments, backing 108 is attached to one or more of sidewalls 103a, 103b, 103c and 103d, as well as rib 107. Attaching backing 108 to the sidewalls and ribs is useful to keep backing 108 from extending into dental floss recess 104 and engaging the dental floss positioned therein. Backing 108 can extend into dental floss recess 104 because it is flexible. It is more difficult to dispense the dental floss if it is engaged by backing 108.

In this embodiment, dispenser 100 includes a sleeve 109 carried by dispenser body 101. Sleeve 109 can be carried by dispenser body at many different locations. In this embodiment, sleeve 109 is attached to backing 108 so that backing 108 is positioned between sleeve 109 and dental floss recess 104 and dispenser body 101. In this way, dispenser 100 includes a sleeve which covers a dental floss recess. In this embodiment, sleeve 109 includes first and second opposed side pieces 109a and 109b, which are coupled together along three sides, as shown in FIG. 1.

Sleeve 109 is attached to backing 108 so that backing 108 provides support for sleeve 109. In particular, second side piece 109b is attached to backing 108, as shown in FIG. 1, and the first side piece 109a is away from the removeable backing. Second side piece 109b extends between backing 108 and first side piece 109a, as shown in FIG. 1. It should be noted that sleeve 109 and backing 108 can be a single integral component. However, sleeve 109 and backing 108 are shown as being separate components for simplicity and ease of discussion. It should also be noted that one or more of the sidewalls and ribs can also provide support for sleeve 109. For example, any combination of dental floss recess sidewall 106, sidewalls 103a, 103b, 103c, 103d and rib 107 can be coupled to sleeve 109 through backing 108 to provide sleeve 109 with support. It should be noted that, in some embodiments, backing 108 and sleeve 109 can be detached from dispenser body 101 so that more dental floss can be positioned within dental floss recess 104. In this way, dispenser 100 can be refilled with dental floss.

In this embodiment, the sidewalls and ribs extend from panel 102 towards backing 108. In this way, dispenser body 101 includes a rib extending towards a backing. Further, the sidewalls and ribs extend from panel 102 towards sleeve 109. In this way, dispenser body 101 includes a rib extending towards a sleeve.

In this embodiment, sleeve 109 includes a sleeve opening 110. In this embodiment, sleeve opening 110 extends between first and second opposed side pieces 109a and 109b, as shown in FIG. 1. Sleeve opening 110 is sized and shaped to receive a card 111, as discussed in more detail below with FIGS. 5a and 5b. In this embodiment, card 111 extends between first and second side pieces 109a and 109b when card 111 is received by sleeve opening 110. Sleeve opening 110 can be positioned at many different locations, such as proximate to sidewall 103a, 103b, 103c and 103d. In these embodiments, sleeve opening 110 is positioned proximate to sidewall 103c or 103d. Sleeve opening 110 extends along the sidewall it is positioned proximate to.

Card 111 can be of many different types, such as a business card. Card 111 generally displays indicia. Hence, card 111 can include indicia printed thereon, wherein the indicia corresponds to business and/or personal information. Examples of business information include a business name, business address and business phone number, among other types of information. Examples of personal information includes a person's name, address and phone number, among other types of information. In this embodiment, a single card is shown. However, it should be noted that, in general, one or more cards can be received by sleeve 109. In this way, dispenser 100 can carry one or more cards.

In this embodiment, sleeve 109 includes a sleeve cut-out 112 positioned proximate to the sleeve opening 110. In this embodiment, sleeve cut-out portion 112 extends through first side piece 109a, as shown in FIG. 1. Sleeve cut-out 112 is useful to remove card 111 from sleeve 109. Sleeve cut-out 112 can have many different shapes. In this embodiment, sleeve cut-out 112 is rounded to allow a finger to extend therethrough, wherein the finger can engage card 111 within sleeve 109. The finger can be moved to pull card 111 out of sleeve 109.

Figure 4:
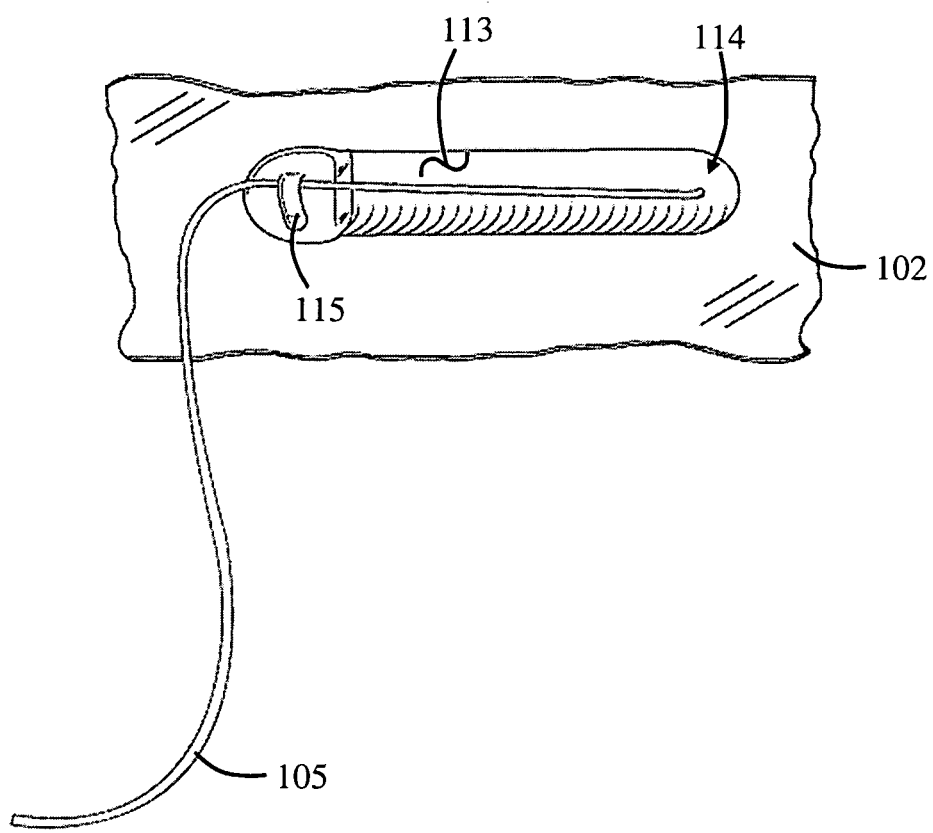
FIG. 4 is a bottom side view of the dispenser body of FIG. 3, wherein the dispenser body includes a panel with a blade recess.

FIG. 4 is a bottom side view of dispenser body 101 showing panel 102. In this embodiment, dispenser body 101 includes blade recess 113 which extends through dental floss recess 104 towards backing 108, as shown in FIGS. 1 and 3. Further, dispenser body 101 includes blade recess 113 which extends through dental floss recess 104 towards sleeve 109. Blade recess 113 can be positioned at many different locations. In this embodiment, blade recess 113 extends through panel 102 and dental floss recess 104. It should be noted that dental floss 105 is generally positioned within dental floss recess 104 so it extends around blade recess 113. Dental floss 105 is generally positioned within dental floss recess 104 so it extends between dental floss recess sidewall 106 and blade recess 113. In this way, dental floss 105 is bounded by blade recess 113 and dental floss recess sidewall 106.

In this embodiment, dispenser 100 includes a dental floss opening 114. Dental floss opening 114 can be positioned at many different locations. In this embodiment, dental floss opening 114 is positioned so it extends through blade recess 113. In general, dental floss opening 114 is positioned so allow dental floss 105 to extend therethrough. In this way, dental floss 105 can be dispensed from dental floss recess 104 by dispenser 100.

In this embodiment, dispenser 100 includes a dental floss blade 115 positioned proximate to blade recess 113. Dental floss blade 115 is useful to cut the dental floss that is dispensed by dispenser 100. In particular, dental floss blade 115 is useful to cut the portion of dental floss 105 that extends through dental floss opening 114. The dental floss typically extends through blade recess 113 and between dental floss blade 115 and dental floss opening 114.

Dental floss blade 115 can be positioned proximate to blade recess 113 in many different ways. In this embodiment, a dental floss blade notch 116 is positioned so it extends through blade recess 113. Dental floss blade 115 includes an arm (not shown) which extends through dental floss blade notch 116. In this way, dental floss blade 115 is coupled to dispenser body 101.

Figure 5A:
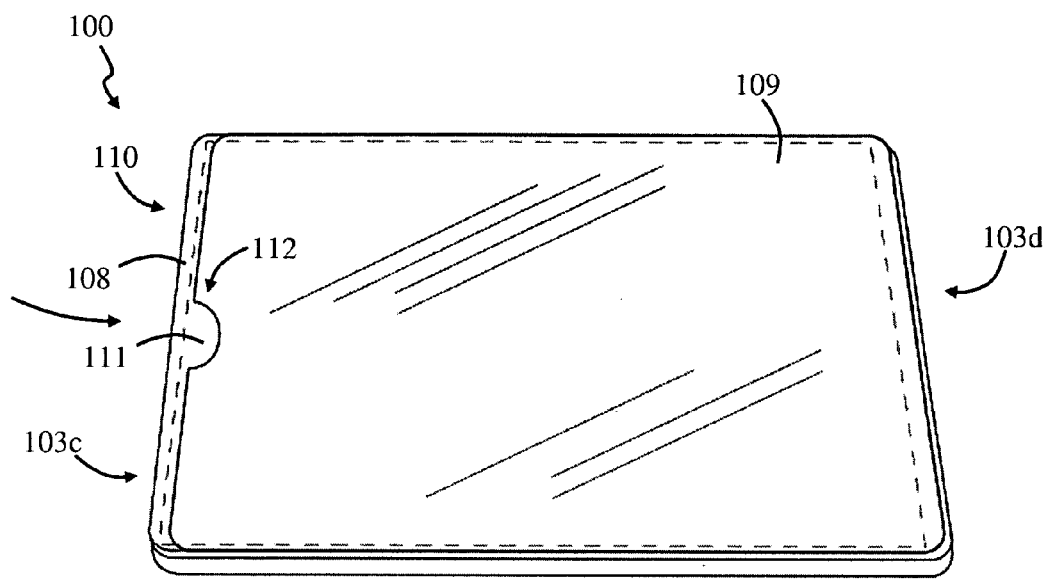
FIG. 5a is a top perspective view of the dispenser of FIG. 1 showing a card in an enclosed condition with a sleeve.
Figure 5B:
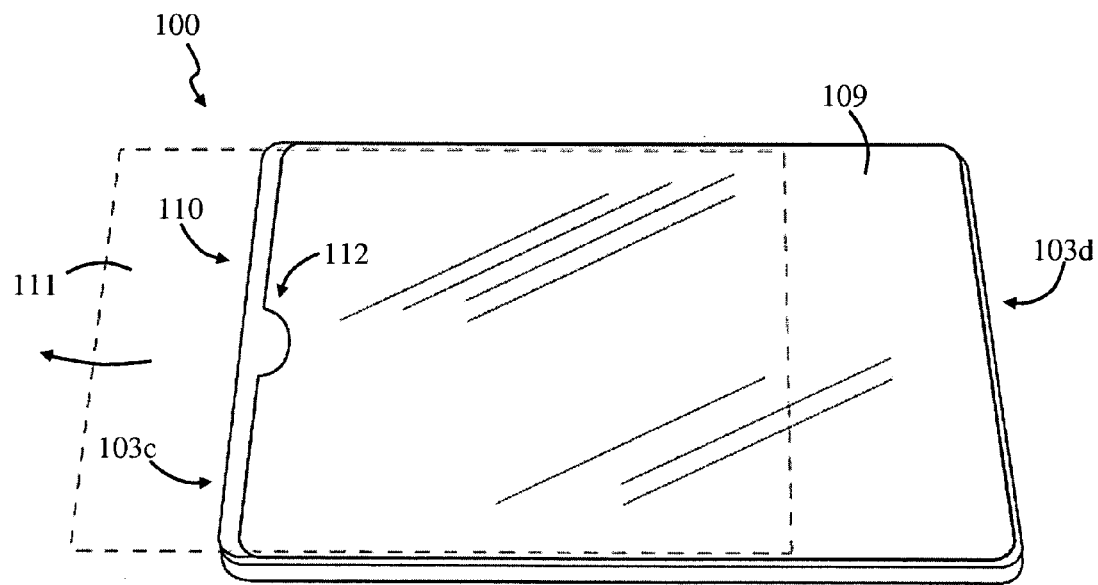
FIG. 5b is a top perspective view of the dispenser of FIG. 1 showing a card in an unenclosed condition with a sleeve.

FIG. 5a is a top perspective view of dispenser 100 showing card 111 in an enclosed condition with sleeve 109, and FIG. 5b is a top perspective view of dispenser 100 showing card 111 in an unenclosed condition with sleeve 109. Card 111 is repeatably moveable through sleeve 109. In particular, card 111 is repeatably moveable through sleeve opening 110. In this embodiment, sleeve opening 110 is positioned proximate to sidewall 103c. Hence, in this embodiment, card 111 is in the enclosed condition when it is moved through sleeve opening 110 towards sidewall 103d. Further, card 111 is in the enclosed condition when it is moved through sleeve opening 110 so that it is positioned between sidewalls 103a, 103b, 103c and 103d. Card 111 is in the unenclosed condition when it is moved through sleeve opening 110 and away from sidewall 103d. Further, card 111 is in the unenclosed condition when it is moved through sleeve opening so it extends over sidewall 103c. Hence, card 111 is in the unenclosed condition when it is not positioned between sidewalls 103c and 103d. In this way, card 111 is repeatably moveable between enclosed and unenclosed conditions with sleeve 109.

Figure 6A:
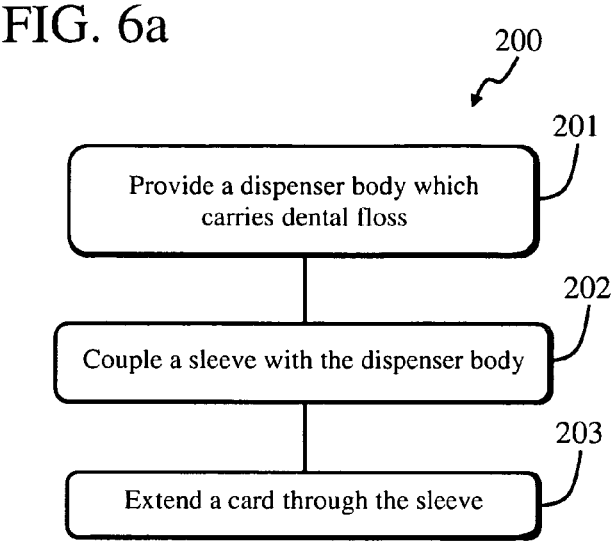
FIGS. 6a and 6b are methods of manufacturing a dispenser, in accordance with the invention.

FIG. 6a is a flow diagram of a method 200, in accordance with the invention. In this embodiment, method 200 includes a step 201 of providing a dispenser body which carries dental floss, and a step 202 of coupling a sleeve with the dispenser body. Step 202 of coupling the sleeve with the dispenser body can include coupling the sleeve with a rib of the dispenser body. Step 202 of coupling the sleeve with the dispenser body can include coupling the sleeve with a dental floss recess sidewall. Method 200 includes a step 203 of extending a card through the sleeve. In some embodiments, step 203 of extending the card through the sleeve includes extending the card through a sleeve opening.

Method 200 can include many other steps. For example, in some embodiments, method 200 includes providing a blade for cutting the floss, wherein the floss is positioned between the blade and card. Method 200 can include positioning a backing between the dispenser body and sleeve. The step of positioning the backing can include coupling the backing with a rib of the dispenser body. The step of positioning the backing can include coupling the backing with a dental floss recess sidewall of the dispenser body.

Figure 6B:
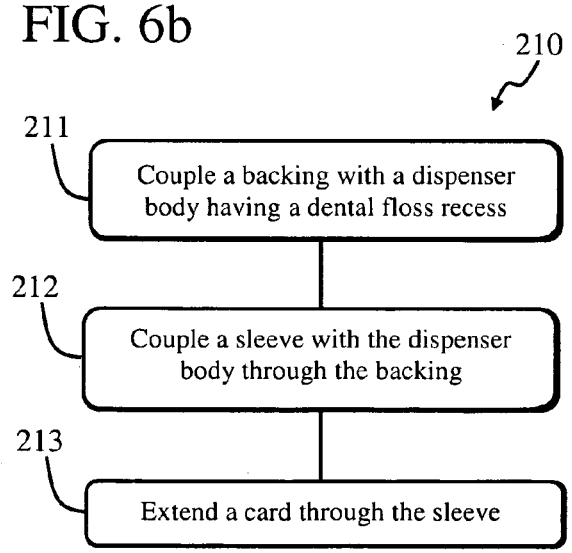

FIG. 6b is a flow diagram of a method 210, in accordance with the invention. In this embodiment, method 210 includes a step 211 of coupling a backing with a dispenser body having a dental floss recess. The dispenser body typically carries dental floss in the dental floss recess. Step 211 of coupling the backing with the dispenser body can include coupling the backing with a rib of the dispenser body. Step 211 of coupling the backing with the dispenser body can include coupling the backing with a dental floss recess sidewall of the dispenser body.

Method 200 includes a step 212 of coupling a sleeve with the dispenser body through the backing. Step 212 of coupling the sleeve with the dispenser body through the backing can include coupling the sleeve with the backing using an adhesive. Method 210 includes a step 213 of extending a card through the sleeve. It should be noted that, in some embodiments, step 213 can include extending more than one card through the sleeve. In some embodiments, step 213 of extending the card through the sleeve includes extending the card through a sleeve opening.

The method 210 can include many other steps. For example, in some embodiments, method 210 includes providing a blade for cutting the dental floss, wherein the dental floss is positioned between the blade and card.

In some embodiments, method 210 includes a step of removing the card from the sleeve. In the embodiments in which multiple cards are enclosed by the sleeve, method 210 can include one or more steps of removing a card from the sleeve. The cards are typically removed from the sleeve one at a time. The card can be removed from the sleeve in many different ways, such as by pulling it out. The card can be pulled out of the sleeve in many different ways. In some embodiments, the sleeve includes a sleeve cut-out which allows a user to engage the card and pull it out of the sleeve. In other embodiments, the sleeve includes opposed sleeve openings, and the card can be pulled through one sleeve opening or pushed through the opposed sleeve opening.

The embodiments of the invention described herein are exemplary and numerous modifications, variations and rearrangements can be readily envisioned to achieve substantially equivalent results, all of which are intended to be embraced within the spirit and scope of the invention.

The invention claimed is:

1. A method, comprising:
providing a dispenser body which carries a reloadable dental floss, wherein the reloadable dental floss extends annularly around a blade recess, wherein the blade recess extends through an outer portion of the dispenser body;
adhesively coupling a removeable backing to the dispenser body;
coupling a sleeve with the removeable backing opposite the dispenser body;
extending a card through the sleeve;
depleting the reloadable dental floss;
detaching the removable backing from the dispenser body;
recharging the dispenser body with reloadable dental floss; and
attaching the backing to the dispenser body.

2. The method of claim 1, wherein the step of extending the card through the sleeve includes extending the card through a sleeve opening.

3. The method of claim 1, further including providing a blade for cutting the floss, wherein the floss is positioned between the blade and card.

4. The method of claim 1, wherein the step of coupling the removeable backing with the dispenser body includes coupling the removeable backing with a rib of the dispenser body.

5. The method of claim 1, further including positioning the removeable backing between the dispenser body and sleeve.

6. The method of claim 5, wherein the step of positioning the removeable backing includes coupling the removeable backing with a rib of the dispenser body.

* * * * *